US010653469B2

(12) United States Patent
Gliner

(10) Patent No.: US 10,653,469 B2
(45) Date of Patent: May 19, 2020

(54) ORTHOPEDIC IMPLANT INSTALLATION USING MAGNETICALLY DRIVEN SCREWS

(71) Applicant: Biosense Webster (Israel) Ltd., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 16/120,685

(22) Filed: Sep. 4, 2018

(65) Prior Publication Data

US 2020/0069348 A1    Mar. 5, 2020

(51) Int. Cl.
| | |
|---|---|
| A61B 17/86 | (2006.01) |
| A61B 17/70 | (2006.01) |
| A61F 2/28 | (2006.01) |
| A61F 2/44 | (2006.01) |
| A61B 17/80 | (2006.01) |
| A61B 17/72 | (2006.01) |
| A61B 17/00 | (2006.01) |

(52) U.S. Cl.
CPC .......... *A61B 17/808* (2013.01); *A61B 17/725* (2013.01); *A61B 17/8057* (2013.01); *A61B 17/8635* (2013.01); *A61B 2017/00876* (2013.01)

(58) Field of Classification Search
CPC ............ A61B 17/7071; A61B 17/7016; A61B 17/8685; A61B 17/863; A61B 17/7002; A61B 17/7046; A61B 17/7037; A61B 17/7008; A61B 17/708; A61B 17/725; A61B 17/8057; A61B 17/8635; A61B 17/7216; A61B 2017/00212; A61B 2017/00876; A61B 2017/681; A61F 2/44

USPC .......... 606/62–68, 246–279, 300–328; 623/18.12, 23.45, 23.47; 403/43–48, 403/109.1–109.8

See application file for complete search history.

(56) References Cited

U.S. PATENT DOCUMENTS

| | | | |
|---|---|---|---|
| 6,849,076 B2 | 2/2005 | Blunn et al. | |
| 7,135,022 B2* | 11/2006 | Kosashvili | A61B 17/7216 606/63 |
| 7,753,915 B1 | 7/2010 | Eksler et al. | |
| 8,034,054 B2* | 10/2011 | Griggs | A61B 17/7216 606/63 |
| 8,057,472 B2 | 11/2011 | Walker et al. | |
| 9,974,581 B2* | 5/2018 | Jansen | A61B 17/7275 |
| 9,987,140 B2* | 6/2018 | Ling | A61B 17/866 |

(Continued)

FOREIGN PATENT DOCUMENTS

DE    102013111354 A1    4/2014

OTHER PUBLICATIONS

Fernandes et al., "Influence of Screw Length and Bone Thickness on the Stability of Temporary Implants," Materials, vol. 9, issue 8, Sep. 2015, pp. 6558-6569.

*Primary Examiner* — Pedro Philogene
(74) *Attorney, Agent, or Firm* — Louis J. Capezzuto

(57) ABSTRACT

An orthopedic implant for insertion into a bone includes an implant body and one or more magnetically activated self-tapping screws. The one or more magnetically activated self-tapping screws are prepositioned in the implant body transversally to a longitudinal axis of the implant body. The prepositioned self-tapping screws are configured to rotate under an influence of an externally applied magnetic field so as to protrude into the bone and lock the orthopedic implant in place.

12 Claims, 2 Drawing Sheets

(56) References Cited

U.S. PATENT DOCUMENTS

| | | |
|---|---|---|
| 10,016,220 B2 * | 7/2018 | Culbert .............. A61B 17/7071 |
| 2008/0086145 A1 | 4/2008 | Sherman et al. |
| 2010/0094305 A1 | 4/2010 | Chang et al. |
| 2011/0060336 A1 | 3/2011 | Pool et al. |

* cited by examiner

ORTHOPEDIC IMPLANT INSTALLATION USING MAGNETICALLY DRIVEN SCREWS

FIELD OF THE INVENTION

The present invention relates generally to orthopedic implants, and particularly to systems and methods for the installation of intramedullary nails.

BACKGROUND OF THE INVENTION

Treatment of orthopedic conditions with implants, such as placing intramedullary nails to secure fractured bones together, as well as managing other orthopedic disorders using implants, were previously proposed. For example, U.S. Patent Application Publication 2008/0086145 describes a system that enables targeting of an instrument placed within a drill bushing, to align the axis of a drill bushing with the axis of a transverse hole in an intramedullary nail. The system includes a probe having an elongated member with a distal end, a magnet that is polarized along its longitudinal axis that is mounted perpendicularly to the distal end of the elongated member; and a processor executing programmed instructions to determine a position and orientation of the magnetic sensor array with respect to the targeting magnet.

As another example, U.S. Patent Application Publication 2010/0094305 describes a spinal distraction system, which according to one embodiment, includes an adjustable spinal distraction rod comprising first and second members. The adjustable spinal distraction rod is configured for non-invasive elongation of the first and second members. The system includes an anchor rod configured for mounting to a bone of a subject, the anchor rod comprising a threaded portion and a ball disposed at one end thereof and a nut disposed on the threaded portion of the anchor rod the nut having a first contact surface. The system further includes a locking joint having a cup portion configured to receive an end of the first member, the cup portion comprising a second contact surface, wherein tightening of the nut binds the first and second contact surfaces to thereby lock the joint and prevent articulation and wherein the second member is configured for mounting to a second bone of a subject.

U.S. Patent Application Publication 2011/0060336 describes an intramedullary lengthening device that includes a housing and a distraction shaft. The intramedullary lengthening device is placed within a cavity of two bone sections (either already separated or purposely separated for insertion of the device). The distraction shaft of the intramedullary lengthening device is attached to the one of the bone sections using, for example, one or more attachment screws. The housing of the intramedullary lengthening device is attached to the second bone section using, for instance, one or more attachment screws. Over the treatment period, the bone is continually distracted, creating a new separation into which osteogenesis can occur. In one embodiment, the intramedullary lengthening device includes an actuator and an extension rod, which can be attached to one other.

U.S. Pat. No. 8,057,472 describes a method of treating scoliosis in a subject that includes securing a scoliosis treatment device to first and second locations on the subject's skeletal system. The scoliosis treatment device includes a first portion, a second portion moveably mounted relative to the first portion, and an adjustment device disposed on the device and configured to change a distraction force between the first location and the second location. The adjustment device includes a rotationally mounted magnetic element configured to move the second portion relative to the first portion in response to rotation of the magnetic element. An external adjustment device is provided external to the subject and is able to adjust the distraction force between the first location and second location.

U.S. Pat. No. 7,753,915 describes bone length adjustment method and system that includes a two-part telescopic device connected to bone parts whose length between the connection points is to be adjusted, with each part of the telescopic device being secured to the bone part, and a rod with an embedded permanent magnet which is in threaded engagement at one or both of its ends with one or both of the parts of the telescopic device. The permanent magnet in the rod is excited by an external solenoid arrangement to cause a radial force to develop at the rod thereby causing it to rotate. Rotation of the rod is converted via the threads at one or both of its ends to axial motion or movement of the telescopic parts relative to each other and thereby causes an increase or decrease in the bone length depending on the direction of axial movement between the telescopic parts.

SUMMARY OF THE INVENTION

An embodiment of the present invention provides an orthopedic implant for insertion into a bone. The implant includes an implant body and one or more magnetically activated self-tapping screws. The one or more magnetically activated self-tapping screws are prepositioned in the implant body transversally to a longitudinal axis of the implant body, and the prepositioned self-tapping screws are configured to rotate under an influence of an externally applied magnetic field so as to protrude into the bone and lock the orthopedic implant in place.

In some embodiments, the orthopedic implant further includes a screw thread, and a screw among the self-tapping screws is pre-threaded into the screw thread and is configured to rotate against the screw thread, so as to protrude into the bone.

In some embodiments, the orthopedic implant further includes an elastic element, which is configured to exert force on a screw among the self-tapping screws in a transversal direction against the bone.

In an embodiment, the orthopedic implant includes an intramedullary nail.

In another embodiment, the orthopedic implant includes an orthopedic plate.

In some embodiments, at least one of the magnetically activated screws includes one or more magnets that are mechanically coupled to the screw and induce perimetrically alternating magnet poles.

In some embodiments, at least one of the screws is configured to be rotated with a preset maximal torque value.

There is additionally provided, in accordance with an embodiment of the present invention, a method including inserting into a bone an orthopedic implant that includes an implant body. One or more magnetically activated self-tapping screws, which are prepositioned in the implant body transversally to a longitudinal axis of the implant body, are rotated using an externally applied magnetic field, so as to cause the screws to protrude into the bone and lock the orthopedic implant in place.

The present invention will be more fully understood from the following detailed description of the embodiments thereof, taken together with the drawings in which:

DETAILED DESCRIPTION OF EMBODIMENTS

Overview

Figure 1:
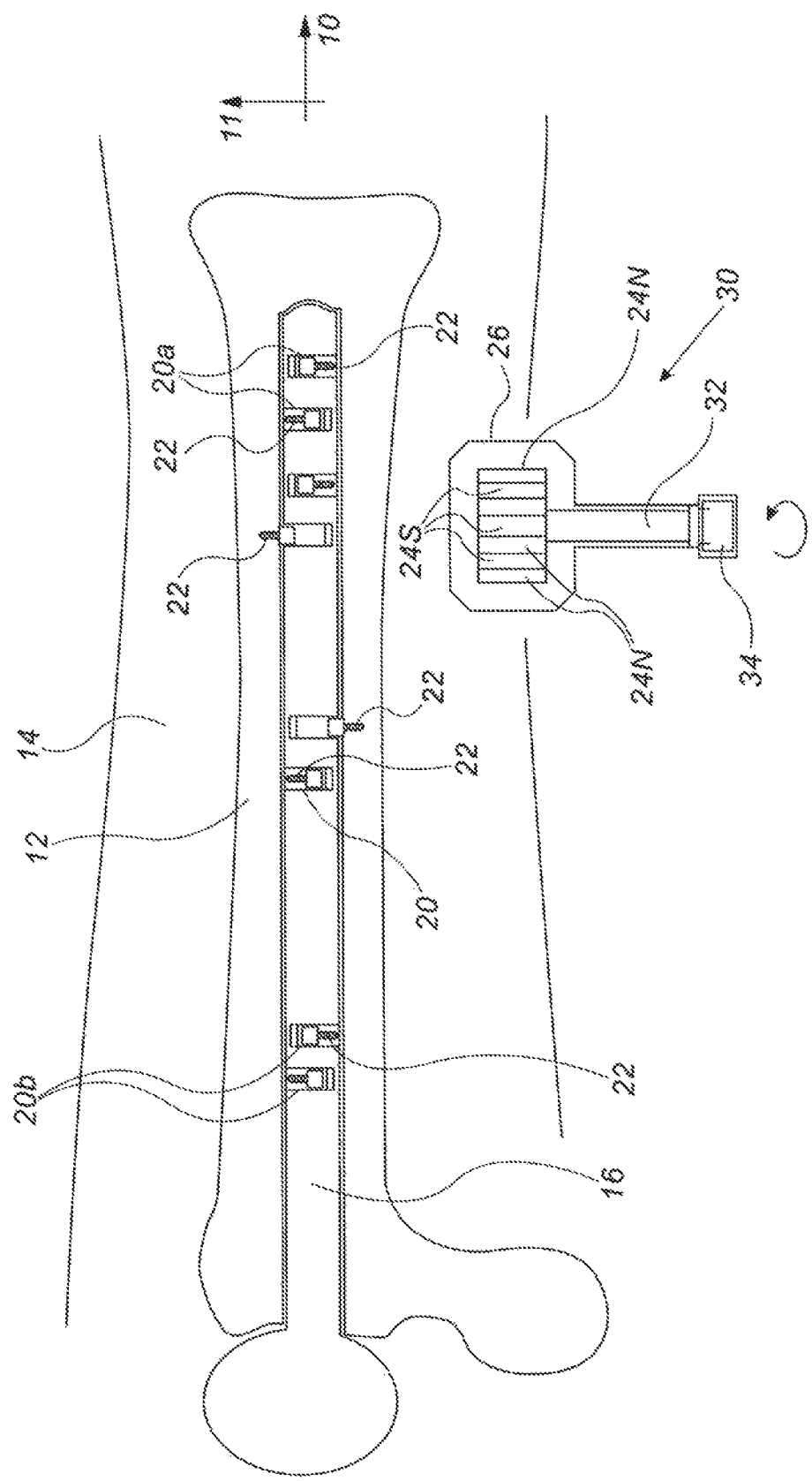
FIG. 1 is a schematic, cross-sectional view of an intramedullary nail-securing apparatus comprising an intramedullary nail, in accordance with an embodiment of the present invention.

Various orthopedic injuries, such as fractured bones, require orthopedic implants, such as nails, in order to secure the injured bone as part of the healing process. In order to lock the implant (e.g., an orthopedic nail) in place after the nail has been inserted into a bone, locking screws may be inserted into the nail in a transverse direction relative to a longitudinal axis of the implant (e.g., perpendicularly to a long axis of a nail). The locking screws may be inserted into receiving holes in the nail from the outside, meaning the screws pass through bone and soft tissue.

In practice, however, accurate drilling of a transverse hole is difficult, especially at the distal end of the nail, since, upon insertion, the nail may bend by an unknown amount. In many cases multiple drilling attempts may be required before a satisfactory hole is formed. Moreover, inserting the screws from the outside, through skin and muscle tissue, presents medical risks, such as hemorrhage and infection.

Embodiments of the present invention that are described hereinafter provide an improved orthopedic implant, such as an orthopedic nail, and an apparatus and method for securing such an implant in a bone. In some embodiments, the orthopedic implant comprises one or more magnetically activated self-tapping screws (i.e., self-drilling screws) that are oriented transversally to the longitudinal axis of the implant. In the present context, the term "transversally" denotes any angle that is not parallel with the longitudinal axis of the implant.

Before the orthopedic implant is placed in a bone (e.g., before the nail is inserted into a bone), the screws do not protrude from the external surface of the implant. Once the orthopedic implant (e.g., the nail) is in place (e.g., in the bone), a physician rotates the prepositioned screws by applying an externally rotating magnetic field generated by an electromagnetic screwdriver (i.e., magnetic driver) comprising perimetrically alternating magnetic poles. The rotated screws exit the orthopedic implant (e.g., the nail), and screw themselves into a surrounding cancellous bone and, to some extent, into an outer cortical bone tissue, thus locking the orthopedic nail in place.

As noted above, as the self-tapping screw is rotated, the screw self-screws itself first into the cancellous bone layer, which is spongy (having typical density of less than 0.2 g/cm$^3$). The required torque to rotate a screw into the spongy bone is minimal. As the screw self-screws itself into the denser outer cortical bone layer, the required torque typically increases, up to several Nm. However, carful design of the screws limits the torque to sub Nm values, as described, for example, by Fernandes et al., in "Influence of Screw Length and Bone Thickness on the Stability of Temporary Implants," Materials, volume 9, issue 8, September, 2015, pages 6558-6569.

In some embodiments, the pitch and diameter of each screw, combined with the number of screws used, are designed as to secure the implant at place with minimal use of torque.

In some embodiments, for a given screw, the implant comprises a housing containing the screw. The screw is pre-threaded into a screw thread in the housing, to facilitate its screwing outside the housing. In an alternative embodiment, the housing comprises an elastic element, such as a spring, which is pressed against the self-tapping screw, constantly pushing the self-tapping screw in a transverse direction against the bone as the screw rotates, so as to assist the self-tapping screw to screw itself into bone.

In some embodiments, the screw includes one or more fixed magnets which induce perimetrically alternating magnet poles, and which are mechanically coupled to the screw head. An external rotating magnetic field, created by a magnetic driver, applies a magnetic torque on the fixed magnets of the screw, thereby forcing the screw to rotate and to screw itself into the bone (i.e., to protrude into the bone). The screw thread is made of a biocompatible material, such as titanium.

In some embodiments the magnets in the screw force the screw to rotate by stepwise hammering one or more arm extensions of the screw head so as to rotate the screw in a stepwise manner. The accumulation of the impact of the hammering steps results in full rotation of the screw into the bone. The stepwise hammering is particularly useful at a later stage of the screwing—when the screw enters the denser cortical bone layer.

In some embodiments, the externally rotating magnetic field is achieved by rotating a rotor of the magnetic driver, which is made of fixed magnets that induce the perimetrically alternating magnet poles. In another embodiment, the rotor is made of one or more electromagnets. In yet another embodiment, the rotating perimetrically alternating magnetic poles are generated by a synchronized modulation of electromagnets, i.e., using electromagnets and without moving parts.

In an embodiment, the magnetic driver head is provided inside a case, and the case is attached externally to the skin of a patient several centimeters from a screw in the nail implant. A rotor of the magnetic driver head is then rotated (inside the static case), for example using an electrical screwdriver with which the screwdriver head is fitted, as described below. When rotated in proximity to the nail, the magnetic rotor applies torque on the screw inside the nail, up to a preset maximal torque value, causing the screw to rotate itself into the bone.

The disclosed technique offers several distinct advantages. First, the disclosed technique does not require drilling holes through skin and muscle tissue, thus avoiding potential complications, such as infections. Second, the disclosed technique does not require accurate alignment of a drilling location with a predrilled hole in the implant, such as a hole in a nail, which might fail and lead to repeated drilling attempts, with risks of bone fractures and infections. Third, the number and distribution of screws can be optimized for the clinical requirement, without the constraints described above. Thus, the disclosed apparatus and technique for installation of an orthopedic implant, such as a nail, using magnetically driven screws, offers both a clinically superior and medically safer orthopedic reconstruction solution than existing techniques.

The disclosed technique can be implemented in types of orthopedic implants other than nails, such as orthopedic plates, that comprise transversally prepositioned magnetically activated screws. The disclosed apparatus and method for securing magnetically activated screws can be implemented, with the requisite changes, with any other type of orthopedic implant.

System Description

FIG. 1 is a schematic, cross-sectional view of an intramedullary nail-securing apparatus, in accordance with an embodiment of the present invention. In some embodiments, an intramedullary nail 16 having a longitudinal axis 10 is inserted into a bone 12, such as a femur bone, to secure broken fragments of bone 12 to one another. Nail 16 comprises magnetically driven self-tapping locking screws 22 inside housings 20 that are prepositioned in the nail along a transverse direction 11. As seen, some of the housings, i.e., housings 20a, are located at a distal part of nail 16, while other housings, e.g., housings 20b, are located more proximally. In an embodiment, the distribution of housings 20 along nail 16 allows fragments to be secured to each other in a clinically optimal manner, as would occur to a person skilled in the art.

A magnetic driver 30 comprises a shaft 32 and an adapter 34 to allow a tool, such as an electrical screwdriver, to rotate shaft 32 so as to rotate magnets 24 inside a housing 26 of driver 30. As seen, magnets 24 induce perimetrically alternating magnet poles 24N and 24S.

When rotated about transverse direction 11, magnets generate a magnetic field that causes self-tapping screws 22 to rotate about direction 11, exit the nail in transverse direction 11, and screw themselves into bone 12, as described below. In the context of the disclosed description a transverse direction 11, is any direction in a plane perpendicular to longitudinal axis 10 (i.e., a radial direction along a perpendicular circle of symmetry about axis 10).

In an embodiment, the length of self-tapping screw 22 is selected such that the screws will not penetrate beyond bone 12 when fully inserted, for example, into a surrounding muscle tissue 14. Only a few of screws 22 are seen in FIG. 1 fully inserted, to exemplify the embodiment.

The cross-sectional view of FIG. 1 is chosen purely for the sake of conceptual clarity. For example, the number of perimetrically alternating magnet poles 24N and 24S included in driver 30 may be larger, or smaller, and their arrangement different than that shown, as would occur to a person skilled in the art. The shape of magnets 24 may be different, so as to optimize coupling of screws 22 such that, for example, comprising magnets poles are separated by a given distance one from another, rather than being adjacent, as seen in FIG. 1. In an embodiment, a step-wise linear actuation of magnets 24 is used, rather than rotation, for coupling of magnetic force to screws 22, for example, by using a linear motor and electromagnets for magnets 24. In another embodiment, a rotating magnetic field comprising perimetrically alternating magnet poles 24N and 24S is generated by a time-varying electrical current applied to electromagnets located inside housing 26.

Nail Installation Technique Using Magnetically Driven Screws

Figure 2:
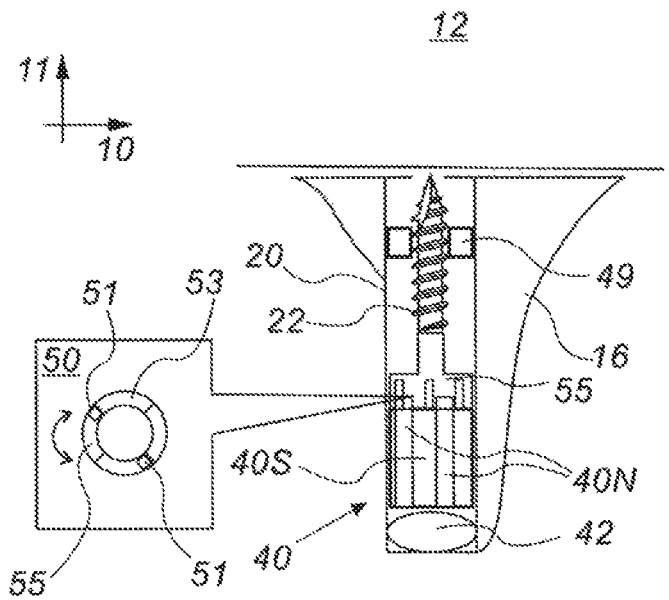
FIG. 2 is a detailed schematic, cross-sectional view of a magnetically driven securing-screw for securing an intramedullary nail, in accordance with an embodiment of the present invention.

FIG. 2 is a detailed schematic, cross-sectional view of a magnetically driven securing-screw for securing an intramedullary nail, in accordance with an embodiment of the present invention. As seen, housing 20 comprises screw having a screw head 55. A magnet 40, comprising perimetrically alternating poles 40S and 40N, is mechanically coupled to rotate self-tapping screw 22. One possible embodiment of such a mechanical coupling is provided in inset 50. As seen in the inset, head 55 comprises apertures 53 through which tenons 51, fixed to magnet 40, are threaded. As further seen, as magnet 40 is forced to rotate (e.g., by an external rotating magnetic field), tenons 51 are pressed against head 55 to generate a preset torque on self-tapping screw 22, so as to cause screw 22 to rotate responsively to magnet 40 rotation. As seen, screws may be rotated in opposing directions by using tenons 51, either to lock the screw in place or to release the screw.

In some embodiments, a housing in the implant contains the screw, wherein the screw is pre-threaded into a screw thread 49 in the housing 20, to facilitate its screwing outside the house in transverse direction 11. In an alternative embodiment, housing 20 comprises an elastic element 42, such as a spring, which is pressed against magnet 40, constantly excreting force on (i.e., pushing) screw head 55 in transverse direction 11 against bone 12 while the screw rotates, so as to assist self-tapping screw 22 to screw itself into bone 12.

The illustration shown in FIG. 2 is chosen purely for the sake of conceptual clarity. For example, magnet 40 may comprise another arrangement and number of poles 40S and 40N. Another mechanical design may be implemented to couple magnet 40 to self-tapping screw 22, and the elastic element may be of a different type than a coiled spring, as would occur to a person skilled in the art.

Other elements may be included, for example, a mechanism to set a maximal torque applied on a screw 22 by magnetic drive 30.

Figure 3:
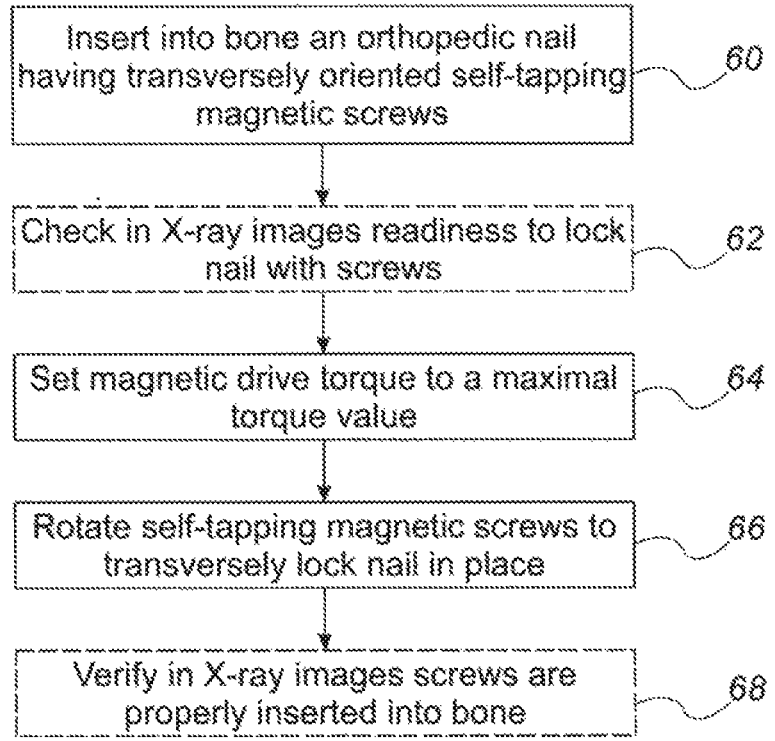
FIG. 3 is a flow chart that schematically illustrates a method for securing an intramedullary nail, in accordance with an embodiment of the present invention.

FIG. 3 is a flow chart that schematically illustrates a method for securing an intramedullary nail, in accordance with an embodiment of the present invention. The process begins with the insertion of intramedullary nail 16, comprising one or more transversely oriented self-tapping magnetic screws 22 into bone 12, at a nail insertion step 60. Next, at an optional inspection step 62, X-ray imaging is used to verify that nail 16 is in place such that self-tapping screws 22 can be rotated to lock the nail. Next, the physician sets a maximal torque at which magnetic drive 30 will rotate a screw 22, at a torque setting step 64. In an optional embodiment, a physician uses the X-ray images acquired in optional step 62 to set a maximal torque value at which each of screws is rotated, so as to minimize risks, such as bone fragmentation. The physician locks nail 16 in place by rotating the magnetically driven self-tapping screws into bone 12 in transverse direction 11, at a nail locking step 66. Finally, at optional X-ray imaging step 68, the physician verifies that the nails sufficiently lock nail 16 in place.

The example flow chart shown in FIG. 3 is chosen purely for the sake of conceptual clarity. For example, in additional embodiments, the physician may decide, based on optional step 68, to rotate other screws that are prepositioned in nail 16 that were unused in step 66.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An orthopedic implant for insertion into a bone, the implant comprising:
   an implant body; and
   one or more self-tapping screws, wherein each screw comprises one or more magnets that are mechanically coupled to the screw and configured to induce perimetrically alternating magnet poles such that the one or more self-tapping screws are magnetically activated, the one or more self-tapping screws being prepositioned in the implant body transversally to a longitudinal axis of the implant body, wherein the one or more self-tapping screws are configured to rotate under an influence of an externally applied magnetic field so as to protrude into a bone and lock the orthopedic implant in place.

2. The orthopedic implant according to claim 1, and comprising a screw thread, wherein a screw among the one or more self-tapping screws is pre-threaded into the screw thread and is configured to rotate against the screw thread, so as to protrude into a bone.

3. The orthopedic implant according to claim 1, and comprising an elastic element, which is configured to exert force on a screw among the one or more self-tapping screws in a transversal direction against a bone.

4. The orthopedic implant according to claim 1, wherein the orthopedic implant comprises an intramedullary nail.

5. The orthopedic implant according to claim 1, wherein the orthopedic implant comprises an orthopedic plate.

6. The orthopedic implant according to claim 1, wherein at least one of the screws is configured to be rotated with a preset maximal torque value.

7. A method comprising:
   inserting into a bone an orthopedic implant that comprises an implant body and one or more self-tapping screws, wherein each screw comprises one or more magnets that are mechanically coupled to the screw and configured to induce perimetrically alternating magnet poles such that the one or more self-tapping screws are magnetically activated, the one or more self-tapping screws being prepositioned in the implant body transversally to a longitudinal axis of the implant body; and
   using an externally applied magnetic field to rotate the one or more so as to cause the one or more self-tapping screws to protrude into a bone and lock the orthopedic implant in place.

8. The method according to claim 7, wherein rotating the screws comprises rotating a screw among the one or more self-tapping screws, which is pre-threaded into a screw thread, against the screw thread so as to protrude into a bone.

9. The method according to claim 7, wherein rotating the screws comprises exerting force on a screw among the one or more self-tapping screws in a transversal direction against a bone using an elastic element.

10. The method according to claim 7, wherein inserting the orthopedic implant comprises inserting an intramedullary nail.

11. The method according to claim 7, wherein inserting the orthopedic implant comprises inserting an orthopedic plate.

12. The method according to claim 7, wherein rotating the screws comprises rotating at least one of the screws with a preset maximal torque value.

* * * * *